US012564377B2

(12) United States Patent
Sabczynski et al.

(10) Patent No.: US 12,564,377 B2
(45) Date of Patent: Mar. 3, 2026

(54) AUGMENTED REALITY FOR ULTRASOUND EXAMS AT THE POINT-OF-CARE IN COMBINATION WITH MECHANICAL VENTILATION

(71) Applicant: KONINKLIJKE PHILIPS N.V., Eindhoven (NL)

(72) Inventors: Joerg Sabczynski, Hamburg (DE); Roberto Buizza, Eindhoven (NL); Jaap Roger Haartsen, Eindhoven (NL); Rafael Wiemker, Hamburg (DE); Thomas Koehler, Hamburg (DE); Cornelis Petrus Hendriks, Eindhoven (NL); Michael Polkey, London (GB); Nataly Wieberneit, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 130 days.

(21) Appl. No.: 18/143,635

(22) Filed: May 5, 2023

(65) Prior Publication Data

US 2024/0000424 A1     Jan. 4, 2024

Related U.S. Application Data

(60) Provisional application No. 63/357,664, filed on Jul. 1, 2022.

(51) Int. Cl.
| | |
|---|---|
| *A61B 8/00* | (2006.01) |
| *A61B 8/08* | (2006.01) |

(Continued)

(52) U.S. Cl.
CPC ............ *A61B 8/4263* (2013.01); *A61B 8/463* (2013.01); *A61B 8/5261* (2013.01); *A61B 8/54* (2013.01);

(Continued)

(58) Field of Classification Search
CPC ..... A61B 8/4263; A61B 8/463; A61B 8/5261; A61B 8/54; A61B 2090/365;

(Continued)

(56) References Cited

U.S. PATENT DOCUMENTS

| | | | | |
|---|---|---|---|---|
| 2015/0164479 A1* | 6/2015 | Toji | ......................... | A61B 8/463 |
| | | | | 600/440 |
| 2015/0209599 A1* | 7/2015 | Schlosser | ................. | A61B 8/54 |
| | | | | 600/427 |

(Continued)

FOREIGN PATENT DOCUMENTS

| | | | |
|---|---|---|---|
| CN | 113243877 A | * | 8/2021 |

OTHER PUBLICATIONS

CN-113243877 machine translation (Year: 2021).*

(Continued)

*Primary Examiner* — Alexei Bykhovski
(74) *Attorney, Agent, or Firm* — Daniel H. Brean

(57) ABSTRACT

A mechanical ventilation assistance device includes at least one electronic controller configured to receive positional data of a patient; determine a position of an imaging device configured to obtain imaging data of the patient based on the received positional data; and display, on a display device, a representation of the determined position of the imaging device.

14 Claims, 3 Drawing Sheets

(51) Int. Cl.
    *A61M 16/00*         (2006.01)
    *A61B 90/00*         (2016.01)

(52) U.S. Cl.
    CPC ..... *A61M 16/022* (2017.08); *A61B 2090/365*
              (2016.02); *A61B 2090/378* (2016.02)

(58) Field of Classification Search
    CPC ... A61B 2090/378; A61B 6/032; A61B 6/462;
              A61B 6/5247; A61B 2034/2065; A61B
              8/0858; A61B 8/462; A61B 8/4245;
              A61M 16/022; A61M 16/04; A61M
              16/0883; A61M 2016/0015; A61M
              2016/0027; A61M 2016/003; A61M
              2202/0208; A61M 2205/18; A61M
              2205/3306; A61M 2205/3375; A61M
              2205/502; A61M 2205/507; A61M
              2205/52; A61M 2205/584; A61M
              2230/432; A61M 2230/62; A61M
              2230/63; A61M 16/024; G16H 30/20;
              G16H 50/50; G16H 30/40; G16H 40/63
    See application file for complete search history.

(56)                References Cited

U.S. PATENT DOCUMENTS

| | | | | |
|---|---|---|---|---|
| 2018/0286518 A1* | 10/2018 | Raju | .................... | A61B 5/4848 |
| 2020/0069285 A1* | 3/2020 | Annangi | ................ | A61B 34/10 |
| 2020/0113544 A1* | 4/2020 | Huepf | ....................... | G06T 7/60 |
| 2020/0214667 A1* | 7/2020 | Shoudy | ................ | A61B 8/4455 |
| 2022/0039864 A1* | 2/2022 | Mckinnon | .............. | A61B 34/25 |
| 2022/0287676 A1* | 9/2022 | Steines | .................. | A61B 6/102 |
| 2024/0285259 A1* | 8/2024 | Kruecker | ............. | A61B 8/5223 |

OTHER PUBLICATIONS

International Search Report for PCT/EP2023/067824 filed Jun. 29, 2023.
Anonymous: "Patient registration—Wikipedia", (Jan. 23, 2022). https://en.wikipedia.org/w/index.php?title=Patient_registration&oldid=1067485573.
Goligher, E.C. et al., "Clinical strategies for implementing lung and diaphragm-protective ventilation: avoiding insufficient and excessive effort", Intensive Care Medicine, vol. 46, No. 12, (Nov. 2, 2020), pp. 2314-2326.
Anonymous: "Endoscopic ultrasound—Wikipedia"; (Jun. 28, 2022). https://en.wikipedia.org/w/index.php?title=Endoscopic_ultrasound&oldid=109547907.
Anonymous: "Endoscopy—Wikipedia", (Jun. 30, 2022). https://en.wikipedia.org/w/index.php?title=Endoscopy&oldid=1095811682.
"Microsoft HoloLens | Mixed Reality Technology for Business." https://www.microsoft.com/en-us/hololens (accessed Apr. 12, 2022).
"Hololens 2," Apr. 03, 2022. Accessed: Apr. 12, 2022. [Online]. Available: https://en.wikipedia.org/w/index.php?title=Hololens_2&oldid=1080722910).
Bolek, K.A. et al., "The effectiveness of the use of augmented reality in anatomy education: a systematic review and meta-analysis," Sci. Rep., vol. 11, No. 1, p. 15292, Dec. 2021, doi: 10.1038/s41598-021-94721-4).
Microsoft Dynamics 365, MSR and Sheba Medical Center meet urgent staffing demands with Hololens 2 and Dynamics 365 Guides, (Jul. 21, 2020). Accessed: Apr. 13, 2022. [Online Video]. Available: https://www.youtube.com/watch?v=glqzAyfSJOQ).
De Witte, N.A.J. et al., "Augmenting Exposure Therapy: Mobile Augmented Reality for Specific Phobia," Front. Virtual Real., vol. 1, p. 8, Aug. 2020, doi: 10.3389/frvir.2020.00008.
Juan, M.C. et al., "Using augmented reality to treat phobias," IEEE Comput. Graph. Appl., vol. 25, No. 6, pp. 31-37, Nov. 2005, doi: 10.1109/MCG.2005.143).
Qian, L. et al., "A Review of Augmented Reality in Robotic-Assisted Surgery," IEEE Trans. Med. Robot. Bionics, vol. 2, No. 1, pp. 1-16, Feb. 2020, doi: 10.1109/TMRB.2019.2957061).
"Augmented reality," Wikipedia. Apr. 12, 2022. Accessed: Apr. 12, 2022. [Online]. Available: https://en.wikipedia.org/w/index.php?title=Augmented_reality&oldid=1082302210.
"Point-of-Care-Ultrasound.jpg (JPEG Image, 400 x 336 pixels)." https://www.medgadget.com/wp-content/uploads/2019/10/Point-of-Care-Ultrasound.jpg (accessed May 1, 2022).
Ruger, C. et al., "Ultrasound in augmented reality: a mixed-methods evaluation of head-mounted displays in image-guided interventions," Int. J. Comput. Assist. Radiol. Surg., vol. 15, No. 11, pp. 1895-1905, Nov. 2020, doi: 10.1007/s11548-020-02236-6.
American Thoracic Society, Thoracic Ultrasonography in the ICU—BAVLS, (May 16, 2017). Accessed: Apr. 22, 2022. Online Video]. Available: https://www.youtube.com/watch?v=rid-AKJY5JI.

\* cited by examiner

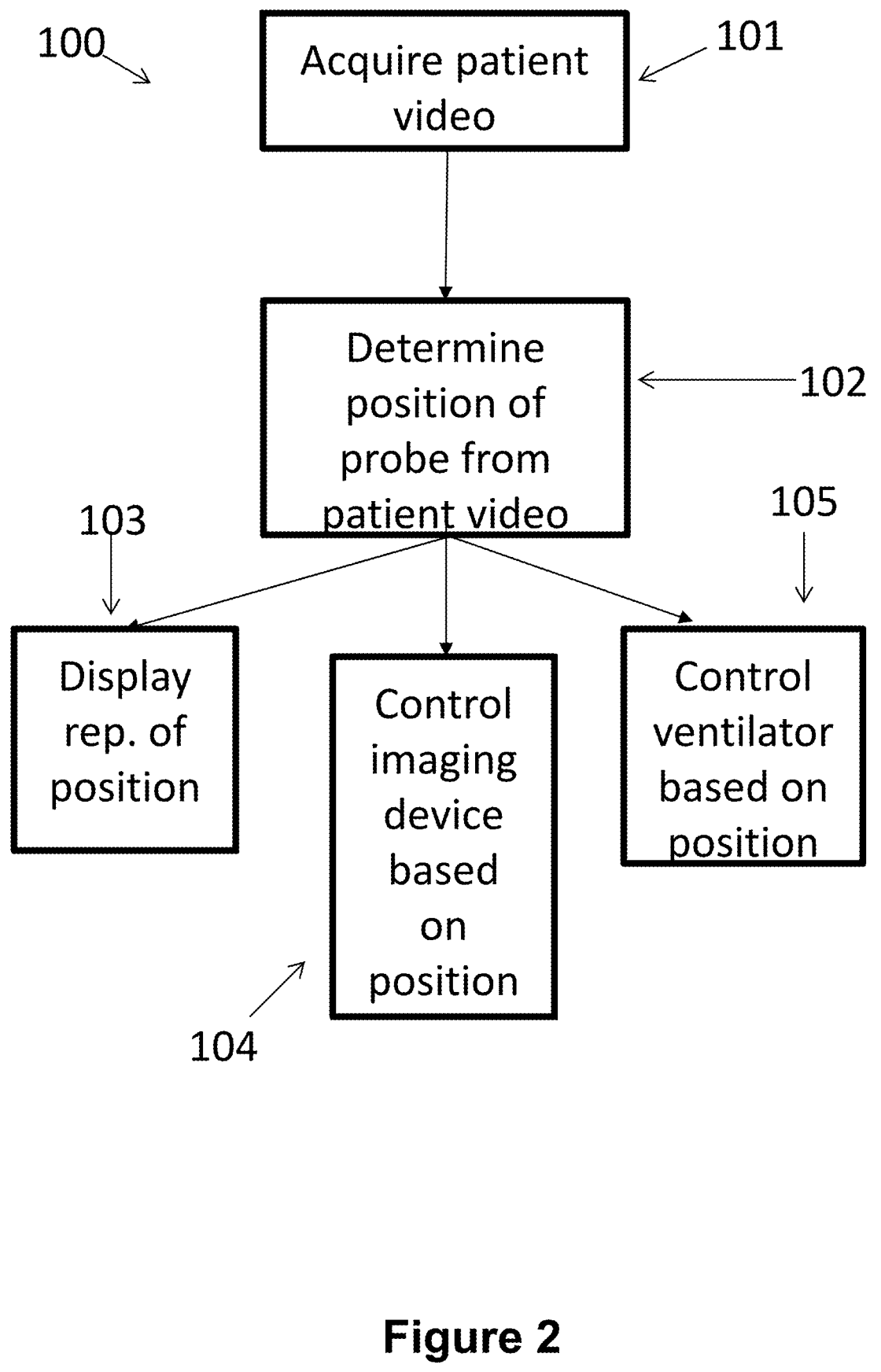

100

Acquire patient video          101

Determine position of probe from patient video          102

103

Display rep. of position

Control imaging device based on position

104

Control ventilator based on position          105

Figure 2

AUGMENTED REALITY FOR ULTRASOUND EXAMS AT THE POINT-OF-CARE IN COMBINATION WITH MECHANICAL VENTILATION

CROSS-REFERENCE TO RELATED APPLICATIONS

This patent application claims the priority benefit under 35 U.S.C. § 119(e) of U.S. Provisional Application No. 63/357,664, filed on Jul. 1, 2022, the contents of which are herein incorporated by reference.

The following relates generally to the respiratory therapy arts, mechanical ventilation arts, mechanical ventilation monitoring arts, ventilator induced lung injury (VILI) arts, mechanical ventilation weaning arts, augmented reality arts, imaging device positioning arts, and related arts.

BACKGROUND

Augmented reality (AR) can be used to augment objects in the real world with computer-generated graphical information. In a typical AR setup, a user wears a head-mounted display which allows the user to see virtual, computer-generated content together with real objects from the real world. This contrasts with virtual reality (VR), which immerses the user in a completely virtual world (i.e., VR exists entirely apart from the real world) while AR tries to combine the real world with computer generated virtual objects. In medicine, a medical practitioner (e.g., a surgeon, doctor, or nurse) can intuitively see virtual objects in his or her field of view while interacting with a patient.

A typical AR system has three main components: a display, a tracking device, and a graphics processor. The display shows virtual objects while simultaneously allowing the view onto the real world. Two categories of displays exist—"optical-see-through" displays and "video-see-through" displays. Optical-see-through displays let light from the real-world shine directly into the eyes of the user. Virtual objects are usually added to the real scene with help of semi-transparent display in front of the user's eyes. Video-see-through displays are completely opaque; therefore, the user cannot see through them. The view onto the real scene is transmitted to the user with the help of video cameras in front of his or her eyes. The video stream from these cameras is shown on the display, augmented by virtual objects. The tracking device can be a position and orientation tracking device. Since AR is used to interact with an augmented version of the real world, it is crucial to know where the user is in the world, where he or she is looking at, and how real and virtual objects relate to each other. Modern AR systems use three-dimensional (3D) sensors (e.g., time-of-flight cameras combined with color cameras). The graphics processor can include a computer graphics engine to create the virtual content to show to the user, taking into account the input from the position tracking device.

These three components might be combined in a single housing, for example a Microsoft HoloLens 2 (see, e.g., "Microsoft HoloLens|Mixed Reality Technology for Business." https://www.microsoft.com/en-us/hololens (accessed Apr. 12, 2022); "HoloLens 2," Apr. 3, 2022. Accessed: Apr. 12, 2022. [Online]. Available: https://en.wikipedia.org/w/index.php?title=HoloLens_2&oldid=1080722910). The HoloLens 2 has an optical see-through display with integrated eye tracking; spatial tracking and hand tracking is integrated as well. Furthermore, the graphics engine to render computer generated objects and scenes is included in the headset.

Many applications of AR have been proposed and have been implemented already. For example, AR can be used in medical education for teaching anatomy, medical procedures, and so forth (see, e.g., K. A. Bölek, G. De Jong, and D. Henssen, "The effectiveness of the use of augmented reality in anatomy education: a systematic review and meta-analysis," *Sci. Rep.*, vol. 11, no. 1, p. 15292, December 2021, doi: 10.1038/s41598-021-94721-4). AR can be used in interactive manuals, for example guiding inexperienced users with complicated technical equipment (see, e.g., Microsoft Dynamics 365*, MSR and Sheba Medical Center meet urgent staffing demands with HoloLens 2 and Dynamics 365 Guides*, (Jul. 21, 2020). Accessed: Apr. 13, 2022. [Online Video]. Available: https://www.youtube.com/watch?v=glqzAyfSJOQ). AR can also be used in psychology, in particular for phobia treatment with exposure therapy (see, e.g., N. A. J. De Witte, S. Scheveneels, R. Sels, G. Debard, D. Hermans, and T. Van Daele, "Augmenting Exposure Therapy: Mobile Augmented Reality for Specific Phobia," *Front. Virtual Real.*, vol. 1, p. 8, August 2020, doi: 10.3389/frvir.2020.00008; M. C. Juan, M. Alcaniz, C. Monserrat, C. Botella, R. M. Banos, and B. Guerrero, "Using augmented reality to treat phobias," *IEEE Comput. Graph. Appl.* , vol. 25, no. 6, pp. 31-37, November 2005, doi: 10.1109/MCG.2005.143). AR can also be used in surgery and interventions, such as proving a touch-free interaction and guidance with 3D data and computers in a sterile environment (see, e.g., L. Qian, J. Y. Wu, S. P. DiMaio, N. Navab, and P. Kazanzides, "A Review of Augmented Reality in Robotic-Assisted Surgery," *IEEE Trans. Med. Robot. Bionics*, vol. 2, no. 1, pp. 1-16, February 2020, doi: 10.1109/TMRB.2019.2957061).

Moreover, ultrasound imaging data of lungs of a patient allows for qualitative and quantitative assessment of the patient status during mechanical ventilation in the intensive care unit (ICU). Diaphragmatic ultrasonography allows for assessment of diaphragm thickness, strain (rate) and excursion. Diaphragm thickness is a surrogate for respiratory muscle activity and thus respiratory effort. Applications of lung ultrasound can include, for example, assessment of lung aeration, detection of decreased regional ventilation, detection of pneumonia, setting a positive end-expiration pressure (PEEP) value, assessment of antibiotics-induced reaeration, patient weaning, and so forth. Diaphragmatic ultrasound can be used for diaphragm function assessment, atrophy detection, weaning prediction, asynchrony detection, ventilation setting optimization, and proportional ventilation (i.e., non-invasive neurally adjusted ventilatory assist (NAVA) ventilation).

The status of ventilated patients in the ICU is often repeatedly assessed (e.g. daily) using measurements with bed-side ultrasound or X-ray imaging to monitor the disease progression or the onset of ventilator-associated pneumonia. A problem is the reliability and repeatability of the ultrasound assessments when done on a day-to-day basis. To generate clinically meaningful information, it is important to ensure that changes in the images are solely due to changes in the patient and are not induced by changes in the imaging equipment, imaging parameters, or imaging setup. When looking at time series of images it is key that the imaging does not disturb the data. Both bed-side X-ray as well as point-of-care ultrasound (POCUS) depend on the position and orientation of the imaging equipment during imaging.

In addition, aligning a handheld ultrasound probe correctly according to pre-defined position and orientation is a mentally demanding task and prone to mistakes. The same is true for aligning a heavy X-ray tube. Another matter can be the availability of trained sonographers in the ICU, especially in a pandemic (e.g. Covid-19) situation. Also, ultrasound often is not ergonomic for the operator especially in an ICU setting. He or she must look to a monitor which is not where the scan head is placed. This unergonomic working pose can result in fatigue and in work-related musculoskeletal disorders.

Moreover, an immediate and intuitive comparison of disease progression on a series of ultrasound images at the POC without the need to consult an expert or to view images at a dedicated viewing station is desirable. A visualization of clinical information (e.g. patient individual anatomical models, patient history, or biophysical models) can also be desirable.

The following discloses certain improvements to overcome these problems and others.

SUMMARY

In one aspect, a mechanical ventilation assistance device includes at least one electronic controller configured to receive positional data of a patient; determine a position of an imaging device configured to obtain imaging data of the patient based on the received positional data; and display, on a display device, a representation of the determined position of the imaging device.

In another aspect, a mechanical ventilation method includes, with at least one electronic controller, receiving positional data of a patient; determining a position of an imaging device configured to obtain imaging data of the patient based on the received positional data; and displaying, on a display device, a representation of the determined position of the imaging device.

One advantage resides in providing a repeatable process for monitoring a status of a patient undergoing ventilation therapy with imaging data.

Another advantage resides in providing a guide for a user to align an imaging device relative to a portion of a patient to be imaged.

Another advantage resides in providing a guide for sonographers in an ICU to perform imaging of a patient.

Another advantage resides in reducing a risk of clinician fatigue and work-related musculoskeletal disorders.

Another advantage resides in providing an indication of a disease progression without the need to view images at a dedicated viewing station.

Another advantage resides in providing a visualization of clinical information of a patient.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

FIG. 2 shows an example flow chart of operations suitably performed by the apparatus of FIG. 1.

DETAILED DESCRIPTION

Figure 1:
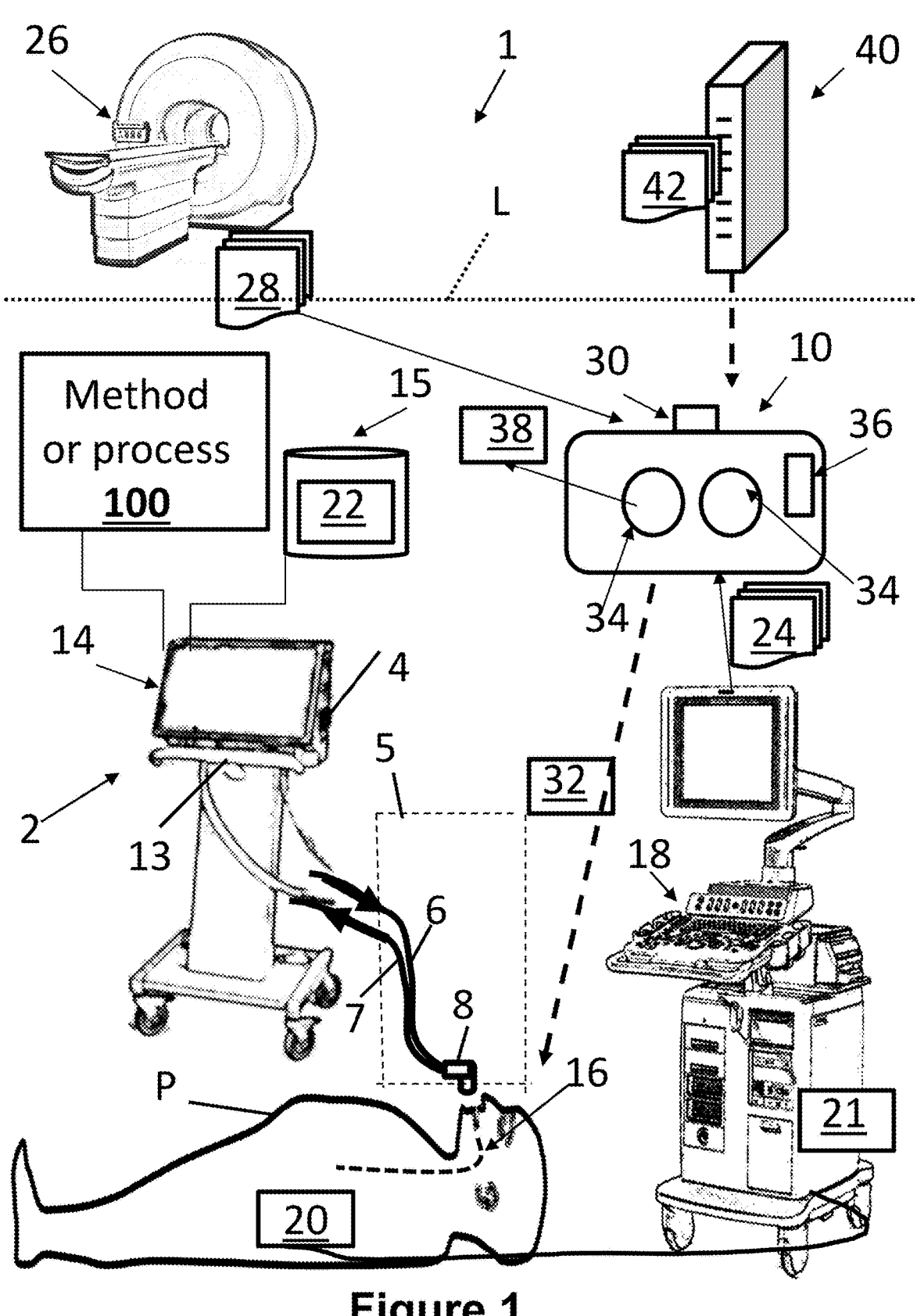
FIG. 1 diagrammatically shows an illustrative mechanical ventilation apparatus in accordance with the present disclosure.

As used herein, the singular form of "a," "an," and "the" include plural references unless the context clearly dictates otherwise. As used herein, statements that two or more parts or components are "coupled," "connected," or "engaged" shall mean that the parts are joined, operate, or co-act together either directly or indirectly, i.e., through one or more intermediate parts or components, so long as a link occurs. Directional phrases used herein, such as, for example and without limitation, top, bottom, left, right, upper, lower, front, back, and derivatives thereof, relate to the orientation of the elements shown in the drawings and are not limiting upon the scope of the claimed invention unless expressly recited therein. The word "comprising" or "including" does not exclude the presence of elements or steps other than those described herein and/or listed in a claim. In a device comprised of several means, several of these means may be embodied by one and the same item of hardware.

With reference to FIG. 1, a mechanical ventilation assistance device 1 is shown. A mechanical ventilator 2 is configured to provide ventilation therapy to an associated patient P is shown. As shown in FIG. 1, the mechanical ventilator 2 includes an outlet 4 connectable with a patient breathing circuit 5 to delivery mechanical ventilation to the patient P. The patient breathing circuit 5 includes typical components for a mechanical ventilator, such as an inlet line 6, an optional outlet line 7 (this may be omitted if the ventilator employs a single-limb patient circuit), a connector or port 8 for connecting with an endotracheal tube (ETT) 16, and one or more breathing sensors (not shown), such as a gas flow meter, a pressure sensor, end-tidal carbon dioxide (etCO$_2$) sensor, and/or so forth. The mechanical ventilator 2 is designed to deliver air, an air-oxygen mixture, or other breathable gas (supply not shown) to the outlet 4 at a programmed pressure and/or flow rate to ventilate the patient via an ETT. The mechanical ventilator 2 also includes at least one electronic processor or controller 13 (e.g., an electronic processor or a microprocessor), a display device 14, and a non-transitory computer readable medium 15 storing instructions executable by the electronic controller 13.

FIG. 1 diagrammatically illustrates the patient P intubated with an ETT 16 (the lower portion of which is inside the patient P and hence is shown in phantom). The connector or port 8 connects with the ETT 16 to operatively connect the mechanical ventilator 2 to deliver breathable air to the patient P via the ETT 16. The mechanical ventilation provided by the mechanical ventilator 2 via the ETT 16 may be therapeutic for a wide range of conditions, such as various types of pulmonary conditions like emphysema or pneumonia, viral or bacterial infections impacting respiration such as a COVID-19 infection or severe influenza, cardiovascular conditions in which the patient P receives breathable gas enriched with oxygen, or so forth.

FIG. 1 also shows an ultrasound (US) medical imaging device 18 that is used to image a portion of the patient P (i.e., a diaphragm). As described herein, the ultrasound medical imaging device 18 is used to acquire ultrasound images or measurement of the patient P. The illustrative embodiments employ brightness mode (B-mode) ultrasound imaging to assess the diaphragm thickness metric. However, other types of ultrasound imaging or data are contemplated, such as motion mode (M-mode) data collected as a single ultrasound line over a time interval, or so forth.

In a more particular example, the medical imaging device 18 includes a handheld ultrasound (US) probe 20. The US probe 20 is positioned to acquire US imaging data (i.e., US images) 22 of the diaphragm of the patient P. For example, the US probe 20 is configured to acquire imaging data of a diaphragm of the patient P, and more particularly US imaging data related to a thickness of the diaphragm of a patient P during inspiration and expiration while the patient P undergoes mechanical ventilation therapy with the mechanical ventilator 2. The electronic processor 13 controls the ultrasound imaging device 18 to receive the ultrasound imaging data 24 of the diaphragm of the patient P from the handheld US probe 20. The ultrasound imaging device 18 can also include a controller or processor 21 (e.g., a microprocessor) configured to control operation of the handheld US probe 20.

Alternatively, the medical imaging device 18 can comprise an X-ray device configured to acquire X-ray images of the patient P (i.e., images of the diaphragm of the patient P). In either embodiment, the medical imaging device 18 is configured to acquire imaging data (e.g., ultrasound (i.e., A-mode ultrasound data, M-mode ultrasound data, three-dimensional (3D) ultrasound data, X-ray data such as 3D reconstructed X-ray images, and so forth).

In the case of a handheld probe 20 used to acquire diaphragm thickness metric values over multiple sessions, e.g. once a day, the clinician operating the ultrasound device 18 will typically attempt to hold the ultrasound probe 20 positioned in the same way respective to the diaphragm of the patient for each measurement. However, in practice there is usually some variation in the position and/or angulation of the ultrasound probe 20 and/or the pressure used to hold it against the patient P from day to day (or more generally from one measurement to the next). It may be that different clinicians perform successive measurements due to varying work shifts and other considerations. Even if the same clinician performs successive measurements some variation in placement of the ultrasound probe 20 is to be expected.

In some embodiments, to compensate for such measurement-to-measurement variations, the non-transitory computer readable medium 15 stores a patient-specific registration model 22 for referencing the ultrasound imaging data 24 (acquired by the medical imaging device 18) to a reference frame. The patient-specific registration model 22 can be used to determine the individual shape of the patient's anatomy based on the acquired ultrasound or X-ray images of the patient P. The patient-specific registration model 22 can also include data related to where the clinician should place the ultrasound probe 20 to follow the clinical protocol for lung examinations or for measurements of the thickening fraction of the diaphragm (TFDI).

The patient-specific registration model 22 can be represented by various mathematical approaches: e.g., as an explicit geometrical model (e.g., organ surface triangle meshes as a function of respiratory phase), or as an implicit ML model (e.g., a deeply layered convolutional or recursive artificial neural network encoder, CNN, RNN, or decision trees, Random Forest, gradient boosting machine), or as a high-dimensional non-linear embedding.

An optional additional imaging device (e.g., a CT imaging device 26 as shown in FIG. 1) may acquire one or more CT images 28 of the patient P, and this may optionally serve as further input for constructing the patient-specific registration model 22. For example, if the model 22 is an explicit geometrical model, then the CT images 28 can be used to construct a patient-specific anatomical model of the specific patient P. It should be noted that the CT imaging device 26 may not be located in the same room, or even the same department, as the mechanical ventilator 2. For example, the CT imaging device 26 may be located in a radiology laboratory while the mechanical ventilator 2 may be located in an intensive care unit (ICU), cardiac care unit (CCU), in a hospital room assigned to the patient P, or so forth. This is diagrammatically indicated in FIG. 1 by separator line L. In such embodiments, the imaging data acquired by the imaging devices 18, 26 can comprise X-ray imaging data, US imaging data, CT imaging data, or any other suitable modality of imaging data.

FIG. 1 also shows an illustrative apparatus or system 10 for acquiring and processing positional data of the patient P. In one example, the positional data can be acquired with an ultrasound device, a mechanical device, an electro-magnetic device (none of which are shown in FIG. 1), or any other suitable device configured to acquire positional data of the patient P.

In some embodiments, the apparatus 10 can comprise, for example, an augmented reality heads-up display (AR-HUD) device (such as a HoloLens device, available from Microsoft Corp. Bellevue, WA, United States) wearable by a clinician (not shown) treating the patient P and configured to acquire the positional data as video data. To acquire the video data of the patient P, the AR-HUD device includes a stereo camera 30 configured to acquire stereo images or video data 32 of the patient P and/or locations of equipment used to treat the patient P within a medical facility. The stereo camera 30 typically includes multiple lenses or lens assemblies with a separate sensor for each lens that forms an image on a digital detector array (e.g. a CCD imaging array, a CMOS imaging array, et cetera) to capture 3D images. The stereo camera 30 preferably (although not necessarily) has color video capability, e.g. by having an imaging array with pixels sensitive to red, green, and blue light (or another set of colors substantially spanning the visible spectrum, e.g. 400-700 nm). The stereo camera 30 optionally may include other typical features, such as a built-in flash (not shown) and/or an ambient light sensor (not shown) for setting aperture, ISO, and/or exposure times. In some examples, a time-of-flight sensor (not shown) can be included with the AR-HUD device 10, and be configured to acquire data to generate a depth map to be used in combination with the video data to generate the positional data of the patient P.

In some embodiments, to determine the exact positions and orientations of objects in space relative to the AR-HUD device 10, an external position and orientation measurement system (not shown) can be implemented to track not only the objects of interest in the scene, but also the AR-HUD device 10. In another example, if the position of the users' eyes is known as well, it is possible to calculate where points in space must be drawn on the display to appear to the user at this position in space. This is then also possible not only for single points but also for complete virtual objects.

The AR-HUD device 10 also includes one or more AR-HUD displays 34. The illustrative design employs left-eye and right-eye displays 34, but alternatively the display can be a single large window that spans both eyes. In some examples, the stereo camera 30 is mounted to the AR-HUD device 10 to provide a "first person view" so as to align the AR content with the actual view seen through the transparent display(s) 34 of the AR-HUD device 10. In some examples, the AR-HUD device 10 can be configured as a helmet, a headband, glasses, goggles, or other suitable embodiment in order to be worn on the head of the user. The stereo camera 30 is mounted to the AR-HUD device 10 (e.g., to overlay the user's forehead, or includes two stereo cameras disposed on lenses of the glasses). A graphical user interface (GUI) can be provided on the displays 34 that overlays graphical content onto the images or videos 32 of the patient P for visualization by the clinician. To provide the GUI and to generate the graphical content, the AR-HUD device 10 includes an electronic controller or processor 36 (e.g., a microprocessor).

FIG. 1 also shows a server computer 40 configured to store one or more historical images 42 of the patient P, or historical images 42 of other patients similar to a clinical trajectory of the patient P. Similar to the CT imaging device 26, the server computer 40 can be located in a different location than the patient P and is shown on an opposing side of the separator line L as shown in FIG. 1 (although this does not necessarily mean that the server computer 40 is disposed in the same location as the CT imaging device 26). In some embodiments, the server computer 40 can store the patient-specific registration model 22.

The non-transitory computer readable medium 15 stores instructions executable by the electronic controller 13 to perform a mechanical ventilation assistance method or process 100.

With reference to FIG. 2, and with continuing reference to FIG. 1, an illustrative embodiment of the mechanical ventilation assistance method 100 is diagrammatically shown as a flowchart. To begin the method 100, the patient P is intubated with the ETT 16 and begins receiving mechanical ventilation therapy from the mechanical ventilator 2. At an operation 101, the positional data 32 of the patient P is acquired, for example as video data 32 acquired by the stereo camera 30 of the AR-HUD device 10, and transmitted to the electronic processor 36 of the AR-HUD device 10. For example, the video data 32 of the patient P can comprise a portion of the patient P to be imaged (i.e., the abdomen of the patient P). In other examples, the video data 32 can include the ultrasound probe 20 (or X-ray device) positioned relative to the patient P (i.e., positioned near or adjacent to the diaphragm of the patient P). The video data 32 can be displayed on the displays 34 of the AR-HUD device 10.

In some embodiments, the video data 32 can be acquired by the patient P. For example, the AR-HUD device 10 can be used by the patient P in a remote setting or home setting. In this case the patient P wears the AR-HUD device 10 and receives guidance information on where to place the ultrasound probe 20. The resulting ultrasound images 24 are stored in a database or transmitted to a medical professional for further examination. If necessary, the position and orientation information on the ultrasound probe 24 relative to the patient P is recorded as well.

At an operation 102, a position of the imaging device 18 (e.g., the ultrasound probe 20, an X-ray device, and so forth) can be determined based on the video data 32. In one example, the determined position of the imaging device 18 can be a current position of the imaging device 18. In another example, the determined position of the imaging device 18 can be a target position of the imaging device 18 (i.e., where the imaging device 18 should be located to image the abdomen of the patient P). This can be performed in a variety of manners. The position and orientation of the ultrasound probe 20 can be continuously tracked and determined. In one embodiment, a position of the ultrasound probe 20 can be determined solely based on the video data 32. For example, the ultrasound images 24 can be acquired by the US probe 20 at a next maximum inhale or maximum exhale of the patient P while the patient P undergoes mechanical ventilation therapy with the mechanical ventilator 2. In another example, the ultrasound images 24 can be acquired by the US probe 20 at multiple positions relative to the anatomy of the patient P.

In another embodiment, one or more ultrasound images 24 of the patient P can be acquired with the ultrasound probe 20, and one or more CT images 28 of the patient P can be acquired by the CT imaging device 26. The ultrasound images 24 and the CT images 28 can be transmitted to the AR-HUD device 10. The electronic processor 36 of the AR-HUD device 10 can then overlay the CT images 28 with the ultrasound images 24, and determine the position of the ultrasound probe 20 based on the CT images 28 overlaid with the ultrasound images 24. In some embodiments, the ultrasound images 24 can comprise 3D ultrasound images, and the 3D ultrasound images (or 2D slices of the 3D ultrasound images) can be overlaid with the CT images 28.

In another embodiment, the patient-specific registration model 22 can be retrieved from the non-transitory storage medium 15, and transmitted to the AR-HUD device 10. The one or more ultrasound images 24 of the patient P can be acquired with the ultrasound probe 20, and also transmitted to the AR-HUD device 10. The electronic processor 36 of the AR-HUD device 10 can then reference the ultrasound images 24 to the patient-specific registration model 22, and then determine the position of the ultrasound probe 20 based on the ultrasound imaging data 24 referenced to the patient-specific registration model 22.

In another embodiment, the one or more historical images 42 can be retrieved from the server computer 40 and transmitted to the AR-HUD device 10. The one or more ultrasound images 24 of the patient P can be acquired with the ultrasound probe 20, and also transmitted to the AR-HUD device 10. The electronic processor 36 of the AR-HUD device 10 can then display a comparison of the current ultrasound images 24 of the patient P with the historical images 42 in order to determine where the ultrasound probe 20 should be positioned to image the diaphragm of the patient P.

At an operation 103, a representation 38 of the determined position of the ultrasound probe 20 can be generated by the electronic processor 36 of the AR-HUD device 10, and displayed on the displays 34 of the AR-HUD device 10. The representation 38 can include, for example, an outline of a "correct" position of the ultrasound probe 20 (i.e., in order to effectively image the diaphragm of the patient P), a comparison of a current position of the ultrasound probe 20 relative to the "correct" position of the ultrasound probe 20, an outline of a position of the diaphragm of the patient P, and so forth.

In some embodiments, the operation 103 can include determining whether a current position of the ultrasound probe 20 matches the representation 38 of a determined target position from the operation 102. To do so, the representation 38 can include a comparison of a current position of the ultrasound probe 20 relative to the target (i.e., "correct") position of the ultrasound probe 20. In one example, an alert can be output on the displays 34 that the current position of the ultrasound probe 20 does not match the representation 38 of the determined target position (i.e., the ultrasound probe 20 is currently positioned incorrectly to image the diaphragm of the patient P), thus allowing the clinician to move the ultrasound probe 20 as needed. In another example, the representation 38 can include visual feedback with instructions for the user to move the ultrasound probe 20 relative to the patient to match the current position of the ultrasound probe 20 to the representation 38 of the target position (i.e., a current position of the ultrasound probe 20 can be outlined in red, and then changed to green once the ultrasound probe 20 is in the "correct" position).

In some embodiments, at an operation 104, the electronic processor 36 of the AR-HUD device 10 can control the ultrasound probe 20 to acquire images 24 of the patient P when the current position of the ultrasound probe 20 matches the representation 38 of the determined target position. To do so, the electronic processor 36 of the AR-HUD device 10 can be in communication with the electronic processor 21 of the medical imaging device 18, and send a signal to the electronic processor 21 of the medical imaging device 18 to acquire images 24 with the ultrasound probe 20. In some embodiments, the medical imaging device 18 can be configured to automatically acquire the ultrasound images 24 only when the current position of the ultrasound probe 20 matches the target position of the ultrasound probe from the representation 38.

In some embodiments, at an operation 105, the electronic processor 36 of the AR-HUD device 10 can control the mechanical ventilator 2 to adjust one or more parameters of mechanical ventilation therapy delivered to the patient P using images 24 acquired of a diaphragm of the patient P when the ultrasound probe 20 is in the determined position. To do so, in one example, a status of the mechanical ventilation therapy can be included in the representation 38 to visualize the status of the mechanical ventilation therapy for the clinician wearing the AR-HUD device 10. In another example, the electronic processor 36 of the AR-HUD device 10 can be in communication with the electronic controller 13 of the mechanical ventilator 2, and send a signal to the electronic controller 13 of the mechanical ventilator 2 to adjust one or more mechanical ventilation settings. In some examples, after the settings of the mechanical ventilator 2 are adjusted, the ultrasound probe 20 can be controlled to acquire additional ultrasound images 24 of the patient P undergoing the updated mechanical ventilation therapy.

During the ultrasound examination, the patient P is continuously ventilated. This leads to chest wall motion as well as to motion of the internal anatomy (lung, liver, diaphragm etc.). If the ultrasound images 24 are compared to the historical images 42 that were captured in different breathing states, it is difficult to judge whether differences in the ultrasound images 24 are due to differences in breathing states or to disease progression. The mechanical ventilator 2 can be set temporarily (for the time of the ultrasound examination) to a predefined and repeatable breathing mode (e.g. with respect to duration and tidal volume). During the recording of the ultrasound images 24, a stream of information from the mechanical ventilator 2 (e.g. information on volume or on breathing phase), along with respiratory muscle activity, can be recorded also. The respiratory muscle activity can be the estimate from the ultrasound images 24 or from other known estimation methods. The information on the breathing phase is analyzed as well. Only those historical images 42 are shown, which are recorded with the same (or approximately the same) breathing phase as the current ultrasound images 24.

It will be appreciated that the operations 103, 104, 105 are not mutually exclusive and can be performed in any suitable order or any suitable combination.

In some embodiments, a remote advisor can also monitor the patient P. Whenever the clinician at the point of care needs advice from a more experienced person (e.g. when faced with difficult problems) the clinician can call a remote adviser. Ideally, the remote adviser is working with VR equipment in a VR environment. This VR environment consists mainly of scene information from the user at the point of care. For the remote adviser, it feels as if he or she is present in the ICU at the point of care together with the local clinician. Gestures and hand motion of the remote adviser in this (virtual) environment can be tracked (e.g., by off-the-shelf VR interaction devices). Therefore, it is possible to overlay guidance information by the remote advisor also in the displays 34 of the AR-HUD device 10. The remote adviser might appear as an avatar or a 3D model in the displays 34 of the AR-HUD device 10.

Figure 3:
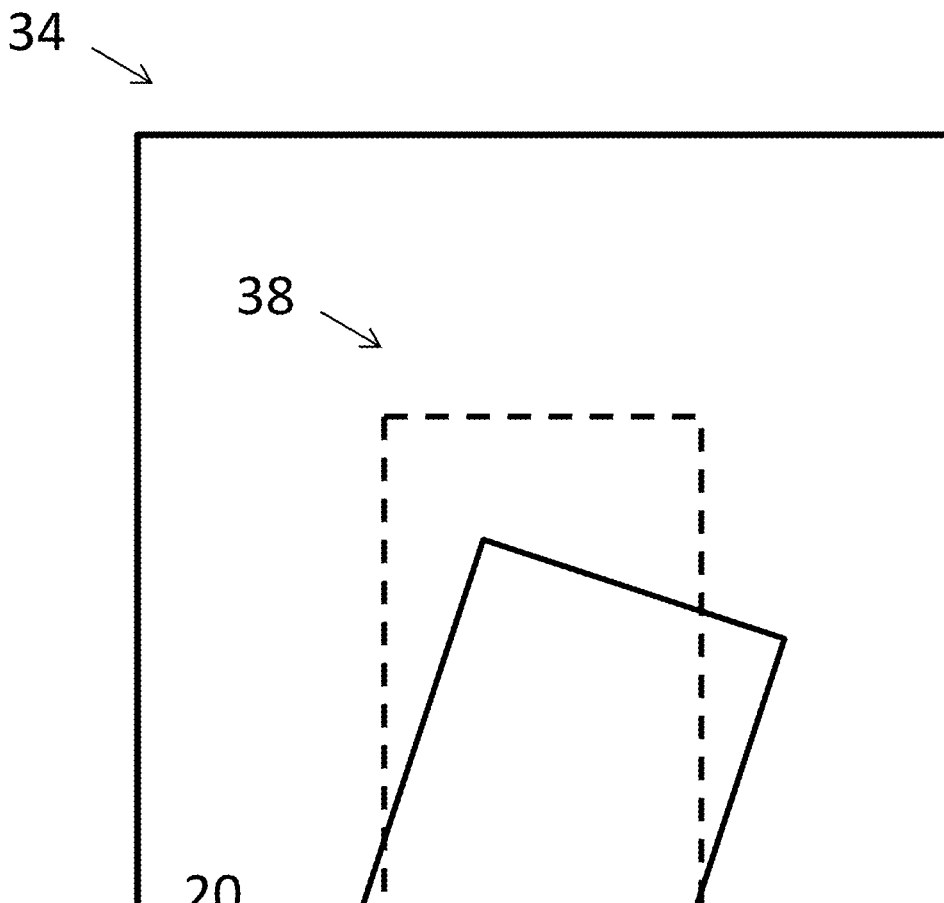
FIG. 3 shows an example representation generated by the apparatus of FIG. 1.

FIG. 3 shows an example of the representation 38 as displayed on the displays 34 (only one of which is shown in FIG. 3) of the AR-HUD device 10. The position of the ultrasound probe 20 (diagrammatically shown in FIG. 3 as a solid rectangle) can be displayed from the live video data 32 acquired by the camera 30 on the displays 34 of the AR-HUD device 10. The representation 38 can comprise the "correct" position that the ultrasound probe 20 should be in to image the diaphragm of the patient P. The representation 38 is diagrammatically shown in FIG. 3 as a dashed rectangle. The clinician can then maneuver the ultrasound probe 20 until the ultrasound probe 20 is in the correct position (i.e., the solid rectangle overlays the dashed rectangle).

The disclosure has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. A mechanical ventilation assistance device comprising at least one electronic controller configured to:
    receive positional data of a patient undergoing mechanical ventilation therapy with a mechanical ventilator;
    determine a position of an imaging device configured to obtain imaging data of the patient based on the received positional data; and
    display, on a display device, a representation of the determined position of the imaging device;
    control the mechanical ventilator to adjust one or more parameters of the mechanical ventilation therapy delivered to the patient using images acquired of a diaphragm of the patient when the imaging device is in the determined position;
    control the imaging device, while in the determined position, to acquire images of the patient in response to the one or more parameters of the mechanical ventilation therapy applied to the patient being adjusted.

2. The device of claim 1, further comprising:
    an augmented-reality heads-up display (AR-HUD) device, wherein the display device comprises at least one lens of the AR-HUD device.

3. The device of claim 2, further comprising:
    a camera attached to a portion of the AR-HUD device; the camera being configured to acquire video data of the patient.

4. The device of claim 1, wherein the imaging data comprises one or more of ultrasound imaging data, X-ray imaging data, or video imaging data.

5. The device of claim 4, wherein the imaging data comprises ultrasound imaging data acquired with an ultrasound probe, and the at least one electronic controller is further configured to:

receive one or more computed tomography (CT) images of the patient;

overlay the one or more CT images with the ultrasound images generated from the ultrasound imaging data of the patient; and determine the position of the ultrasound probe based on the CT images overlaid with the ultrasound images.

6. The device of claim 4, further including:

a non-transitory storage medium storing a patient-specific registration model for referencing the ultrasound imaging data to an anatomy of the patient;

wherein the at least one electronic controller is further configured to determine the position of the imaging device based on the ultrasound imaging data referenced to the patient-specific registration model.

7. The device of claim 4, wherein the imaging data comprises ultrasound imaging data acquired with an ultrasound probe, and the at least one electronic controller is further configured to:

receive one or more historical images of the patient;

overlay the one or more historical images with the ultrasound images generated from the ultrasound imaging data of the patient; and determine the position of the ultrasound probe based on the historical images overlaid with the ultrasound images.

8. The device of claim 1, wherein the imaging device comprises:

an ultrasound probe configured to acquire the imaging data of the patient as ultrasound images.

9. The device of claim 8, wherein the positional data of the patient comprises video data, the determined position of the imaging device comprises a target position of the ultrasound probe, and wherein the at least one electronic controller is configured to:

receive video data of the ultrasound probe positioned relative to the patient;

determine whether a current position of the ultrasound probe matches the representation of the target position.

10. The device of claim 9, wherein the at least one electronic controller is further configured to:

output an alert on the display device that the current position of the ultrasound probe does not match the representation of the target position.

11. The device of claim 10, wherein the at least one electronic controller is further configured to:

provide visual feedback on the display device with instructions for the user to move the ultrasound probe relative to the patient to match the representation of the target position.

12. The device of claim 1, wherein the imaging device comprises an ultrasound probe configured to acquire the imaging data of the patient as ultrasound images, the positional data of the patient comprises video data of the ultrasound probe and the patient, and the at least one electronic controller is configured to:

determine whether a current position of the ultrasound probe matches a target position; and control the ultrasound probe to automatically acquire images of the patient only when the current position of the ultrasound probe matches the target position.

13. The device of claim 1, further comprising:

the mechanical ventilator configured to deliver the mechanical ventilation therapy to the patient.

14. The device of claim 13, wherein the at least one electronic controller is configured to control the imaging device to acquire images of the patient after the one or more parameters of the mechanical ventilator are adjusted.

* * * * *